United States Patent
San et al.

(10) Patent No.: US 10,920,251 B2
(45) Date of Patent: Feb. 16, 2021

(54) MICROBIAL PRODUCTION OF FATS

(71) Applicant: William Marsh Rice University, Houston, TX (US)

(72) Inventors: Ka-Yiu San, Houston, TX (US); Zhilin Li, Houston, TX (US); Xian Zhang, Houston, TX (US)

(73) Assignee: WILLIAM MARSH RICE UNIVERSITY, Houston, TX (US)

(*) Notice: Subject to any disclaimer, the term of this patent is extended or adjusted under 35 U.S.C. 154(b) by 103 days.

(21) Appl. No.: 16/098,914

(22) PCT Filed: May 5, 2017

(86) PCT No.: PCT/US2017/031174
§ 371 (c)(1),
(2) Date: Nov. 5, 2018

(87) PCT Pub. No.: WO2017/192925
PCT Pub. Date: Nov. 9, 2017

(65) Prior Publication Data
US 2019/0144898 A1     May 16, 2019

Related U.S. Application Data

(60) Provisional application No. 62/332,308, filed on May 5, 2016.

(51) Int. Cl.
| | | |
|---|---|---|
| *C12N 1/20* | (2006.01) | |
| *C12P 7/64* | (2006.01) | |
| *C12N 9/02* | (2006.01) | |
| *C12N 15/52* | (2006.01) | |
| *C12N 9/16* | (2006.01) | |
| *C12N 9/88* | (2006.01) | |
| *C12N 9/04* | (2006.01) | |
| *C12N 15/74* | (2006.01) | |

(52) U.S. Cl.
CPC .............. *C12P 7/6409* (2013.01); *C12N 1/20* (2013.01); *C12N 9/0006* (2013.01); *C12N 9/0008* (2013.01); *C12N 9/16* (2013.01); *C12N 9/88* (2013.01); *C12N 15/52* (2013.01); *C12N 15/74* (2013.01); *C12Y 102/01051* (2013.01); *C12Y 102/07001* (2013.01)

(58) Field of Classification Search
CPC .................................................... C12P 7/6409
See application file for complete search history.

(56) References Cited

U.S. PATENT DOCUMENTS

| | | |
|---|---|---|
| 4,762,784 A | 8/1988 | Keith et al. |
| 7,262,046 B2 | 8/2007 | Ka-Yiu et al. |
| 7,326,557 B2 | 2/2008 | San et al. |
| 7,569,380 B2 | 8/2009 | San et al. |
| 7,901,924 B2 | 3/2011 | San et al. |
| 8,129,157 B2 | 3/2012 | Gonzalez |
| 8,486,686 B2 | 7/2013 | Segueilha et al. |
| 8,691,552 B2 | 4/2014 | Gonzalez et al. |
| 8,795,991 B2 | 8/2014 | San et al. |
| 8,962,272 B2 | 2/2015 | San et al. |
| 2010/0317086 A1* | 12/2010 | Segueilha ............. C12P 7/04 435/252.33 |
| 2014/0093921 A1 | 4/2014 | San et al. |
| 2014/0193867 A1 | 7/2014 | San et al. |
| 2014/0212935 A1 | 7/2014 | San et al. |
| 2014/0273114 A1 | 9/2014 | San et al. |
| 2015/0037853 A1 | 2/2015 | Fischer et al. |
| 2015/0259712 A1 | 9/2015 | San et al. |

FOREIGN PATENT DOCUMENTS

WO     2015054138     4/2015

OTHER PUBLICATIONS

Olsson, J., & Andrews, J.F., "The dissolved oxygen profile—A valuable tool for control of the activated sludge process," Water Research, vol. 12, Issue 11, pp. 985-1004 (Mar. 3, 1978).

Sun, Z., et al., "Amino acid substitutions at glutamate-354 in dihydrolipoamide dehydrogenase of *Escherichia coli* lower the sensitivity of pyruvate dehydrogenase to NADH," Microbiology, vol. 158, pp. 1350-1358 (May 2012).

Wu, H., et al., "Metabolic transistor strategy for controlling electron transfer chain activity in *Escherichia coli*," Metabolic Engineering, vol. 28, pp. 159-168 (Mar. 2015).

Zhang, X., et al., "Efficient free fatty acid production in *Escherichia coli* using plant acyl-ACP thioesterases," Metabolic Engineering, vol. 13, Issue 6, pp. 713-722, Nov. 2011.

Tatusova, T.A., and Madden, T.T., "Blast 2 Sequences, a new tool for comparing protein and nucleotide sequences," FEMS Microbiology Letters, vol. 174, pp. 247-250 (1998).

International Search Report & Written Opinion of the International Searching Authority received in Application No. PCT/US2017/031174, dated Jul. 20, 2017.

\* cited by examiner

*Primary Examiner* — Tekchand Saidha
(74) *Attorney, Agent, or Firm* — Boulware & Valoir

(57) ABSTRACT

This invention describes a method of using microbial to produce fats, such as fatty acids and their derivatives, or products derived from the fatty acid synthesis cycle, such as hydroxyfatty acids, methyl ketones, and the like.

9 Claims, 4 Drawing Sheets

ML103(pXZ18Z)

A-1 ML103(pXZ18Z)

A-2 ML103(pXZ18Z)

MICROBIAL PRODUCTION OF FATS

PRIOR RELATED APPLICATIONS

This application claims priority to U.S. Ser. No. 62/332,308, IMPROVED MICROBIAL PRODUCTION OF FATS, filed May 5, 2016, and PCT/US2017/031174, filed May 5, 2017, each of which is incorporated by reference herein in its entirety for all purposes.

FEDERALLY SPONSORED RESEARCH STATEMENT

This invention was made with government support under Grant No: 2012-10008-20263 awarded by the USDA. The government has certain rights in the invention.

FIELD OF THE DISCLOSURE

This invention relates generally to the microbial production of fats, such as fatty acids and their derivatives, or products derived from the fatty acid synthesis cycle, such as hydroxyfatty acids, methyl ketones, and the like.

BACKGROUND OF THE DISCLOSURE

Anaerobic fermentation and aerobic respiration have been the two metabolic modes of interest for the industrial bioproduction of chemicals, such as fats. Oxygen rich respiration offers very efficient cell growth (growth rate and yield) and converts a high percentage of the carbon source into carbon dioxide and cell mass (see Table 1), but typically has low product yields. Anaerobic fermentation, on the other hand, has high product formation, but poor cell growth and the synthesis of several competing fermentation products at high yields (e.g. lactate, formate, ethanol, acetate, succinate, etc.), thus, diverting carbons away from the desired product.

TABLE 1

Respiratory vs fermentative metabolism

| Variable | Anaerobic Fermentation | Anaerobic Respiration | Aerobic Respiration |
|---|---|---|---|
| Growth Rate | LOW | Intermediate | HIGH |
| Cell Mass | LOW | Intermediate | HIGH |
| Product Yields | HIGH | High/Intermediate | LOW |
| Capital Cost | LOW | LOW | HIGH |
| Energy Input | LOW | LOW | HIGH |

Producing chemicals via oxygen rich processes, however, is more costly than using anaerobic methods for two reasons. First, aerobic fermenters are more expensive to build, due to both the higher cost per unit and the need for smaller fermenters with reduced economy of scale. Secondly, the aerobic fermenters are more costly to operate than their anaerobic counterparts due to low solubility of oxygen, which in turn requires high energy input to ensure appropriate supply of oxygen to the cells. This is especially relevant for the production of commodity chemicals, where fermentation costs can represent 50-90% of the total production cost.

Therefore, anaerobic methods are usually preferred where possible, and it is typical to grow cells to a large number aerobically, and then switch the cells to anaerobic culture for the production of desired molecules. Often, however, the method is unsuccessful, resulting in poor yields and rates.

What is needed in the art is a novel culture method that allows high yield and rates of production of compounds, such as fatty acids and their derivatives, yet is amenable to scale up and is cost effective.

SUMMARY OF THE INVENTION

Fatty acids are aliphatic acids fundamental to energy production and storage, cellular structure and as intermediates in the biosynthesis of hormones and other biologically important molecules. Fatty acids in $E.\ coli$, for example, are synthesized by a series of decarboxylative Claisen condensation reactions using acetyl-CoA to add two carbon units to a growing fat. Following each round of elongation the beta keto group is reduced to the fully saturated carbon chain by the sequential action of a ketoreductase, a dehydratase, and an enol reductase.

The growing fatty acid chain is carried between these active sites while attached covalently to the phosphoantetheine prosthetic group of an acyl carrier protein (ACP), and is released from the ACP by the action of a thioesterase (TE) upon reaching a carbon chain length of e.g., 16, although this can be varied by adding different TE enzymes to the cell.

This invention relates to a technology to improve microbial production of fatty acids, fatty acid derivatives and/or products derived from the fatty acid synthesis cycle through the use of a new micro-aerobic/anaerobic cultivation method. The traditional fatty acid production was performed under fully aerobic conditions, because fatty acid production dropped significantly under anaerobic conditions.

There are two main reasons for the absolute requirement of oxygen for high free fatty acid production. One reason is due to the limitation of ATP availability. Only 2 ATP per glucose will be generated in the glycolysis pathway under anaerobic conditions and 1 ATP is required for each fatty acid elongation cycle.

The second reason is due to limited reducing equivalent availability and is more problematic. Under normal aerobic conditions, the conversion of pyruvate to acetyl-CoA, a precursor for fatty acid synthesis, and NAD+ to NADH is carried out by the enzyme pyruvate dehydrogenase (PDH). However, under anaerobic conditions, pyruvate dehydrogenase activity is much reduced and the reaction of converting pyruvate to acetyl-CoA is mainly carried out by the enzyme pyruvate formate lyase (PFL). However, the reaction catalyzed by pyruvate formate lyase does not produce any NADH, but produces formate instead. As such, one glucose molecule can only generate 2 reducing equivalents through the glycolysis pathway. Under these conditions, there is a shortfall in reducing equivalents supply since every fatty acid elongation cycle requires 2 reducing equivalents (2 cycles or 4 reducing equivalents per glucose).

We have overcome these difficulties by developing new culturing methods, as well as new strains that are less limited in reducing equivalents.

One method comprises culturing a bacteria in a growth medium aerobically (e.g., about 40% DO) until sufficient cell mass is obtained, e.g., an OD of >2, >3, >4, >5 or >6 is reached; further culturing said bacteria under oxygen lean conditions (e.g., <5% DO) and sparging the head space (not the media) with air or $O_2$ containing gas until product is formed; and isolating said product from said bacteria, said growth medium or both.

We have also developed a novel genetic background that allows the bacteria to produce high amounts of fat, even when grown anaerobically. This genetic background include at multiple copies of an exogenous NAD-dependent formate dehydrogenase (3×FDH), plus optionally an overexpressed acyl-ACP thioesterase (TE), overexpresssed NAD-dependent fabG gene (FABG) and an added overexpresssed fabZ gene (FABZ). Preferably, the bacteria have at least two or three chromosomally integrated copies of an exogenous NAD-dependent formate dehydrogenase (3×FDH), plus optionally an overexpressed acyl-ACP thioesterase (TE), overexpresssed NAD-dependent fabG gene (FABG) and an added overexpresssed fabZ gene (FABZ). As much as ten or 11 fold increase in fat production was observed with these strains, even when grown without oxygen.

$OD_{600}$ of 1.0 is roughly about $8 \times 10^8$ cells/ml. However, the OD of a sample is dependent on the size and shape of the particles in it, and also on the spectrophotometer. Thus, different cell lines and different machines can have completely different relationships between OD and cells/mL. Thus, the OD readings herein are approximate, and correlate to about 80-90% maximum cell mass before stationary phase is reached.

Another embodiment comprises culturing a bacteria in a growth medium with about 40% DO until an OD of >2, >3, >4, >5, >6 is reached; smoothly transitioning from 30-60% DO, preferably about 40% DO, to 5% DO over a course of time, preferably 1-12 hrs, 2-8 hrs, or about 5 hrs; further culturing said bacteria with about 5% DO and sparging the head space with air until product is formed; and isolating said product from said bacteria, said growth medium or both.

Yet another method comprises culturing a bacteria in a growth medium with about 35-45% DO, or about 40% DO, until sufficient cell mass is obtained; smoothly transitioning from 40% DO to 0.5% DO over a course of time, preferably 1-12 hrs, 2-8 hrs, or about 5 hrs; further culturing said bacteria with <5% or preferably about 0.5% DO sparging the head space with air until product is formed; and isolating said product from said bacteria, said growth medium or both.

Additionally, a method of producing fatty acids in bacteria is provided, comprising culturing a bacteria in a growth medium with a 40% DO until sufficient cell mass is obtained, e.g., at least 75% or about 80-90% of stationary phase growth; smoothly transitioning from 40% DO to 0.5% DO over a course of time, preferably 1-12 hrs, 2-8 hrs, or about 5 hrs; further culturing said bacteria with 350 rpm and sparging the head space with air until fatty acids are formed; and isolating said fatty acids from said bacteria, said growth medium or both.

Further, with certain mutants, the oxygen lean conditions can even be reduced to anaerobic (0% DO). Thus, a method of producing fatty acids in bacteria comprising an NADH-dependent formate dehydrogenase, an NADH insensitive pyruvate dehydrogenase or a pyruvate:ferredoxin oxidoreductase is provided; said method comprising: aerobically culturing a bacteria in a growth medium until >75 to <95% maximum cell mass before stationary phase is reached; simultaneously smoothly transitioning from aerobic to anaerobic or oxygen lean conditions of 0 to <5% DO over a course of time; further culturing said bacteria under anaerobic condition or with oxygen lean conditions (agitation at about 350 rpm and only sparging the head space with air) until fatty acids are formed; and isolating said fatty acids from said bacteria, said growth medium or both.

Many microbes do not make significant amounts of free fatty acids, but can be made to do so by adding overexpressed acyl-ACP thioesterase (called a "TE" herein), which is a promiscuous enzyme that also works on ~coA activated intermediates, as well as ACP-carried intermediates. It is also known to change the chain length of the FFAs by changing the TE. 1) Class I acyl-ACP TEs act primarily on 14- and 16-carbon acyl-ACP substrates; 2) Class II acyl-ACP TEs have broad substrate specificities, with major activities toward 8- and 14-carbon acyl-ACP substrates; and 3) Class III acyl-ACP TEs act predominantly on 8-carbon acyl-ACPs.

For example, most thioesterases exhibit the highest specificities in the C16-C18 range, including *A. thaliana* FatA (18:1Δ9), *Madhuca longifolia* FatB (16:0, 16:1, 18:0, 18:1), *Coriandrum sativum* FatA (18:1Δ9), *A. thaliana* FatB (16:0, 18:1, 18:0, 16:1), *Helianthus annuus* FatA (18:1, 16:1), and *Brassica juncea* FatB2 (16:0, 18:0), among numerous others. Medium-chain acyl-ACP thioesterases include *Cuphea palustris* FatB1 and *C. hookeriana* FatB2 (8:0, 10:0), *C. palustris* FatB2 (14:0, 16:0); and *Umbellularia californica* FatB (12:0, 12:1, 14:0, 14:1). Arecaceae (palm family) and *Cuphea* accumulate large quantities of fatty acids that are shorter (between 8 and 12 carbon atoms), and several enzymes are also available in bacteria. Exemplary thioesterase families and common names of their members are shown in Table 2. Thousands of such sequences are readily available.

TABLE 2

Thioesterase Families and Common Names of their Members

| Family | Producing organisms | Genes and/or other names of family members |
| --- | --- | --- |
| TE1 | A, B, E[a] | Ach1 |
| TE2 | A, B, E | Acot1 - Acot6, BAAT thioesterase |
| TE3 | A, B | tesA, acyl-CoA thioesterase I, protease I, lysophospholipase L1 |
| TE4 | B, E | tesB, acyl-CoA thioesterase II, Acot8 |
| TE5 | B | tesC (ybaW), acyl-CoA thioesterase III |
| TE6 | A, B, E | Acot7 (BACH), Acot11 (BFIT, Them1), Acot12 (CACH), YciA |
| TE7 | B, E | Acot9, Acot10 |
| TE8 | A, B, E | Acot13 (Them2) |
| TE9 | B | YbgC |
| TE10 | B | 4HBT-I |
| TE11 | B | 4HBT-II, EntH (YbdB) |
| TE12 | B, E | DNHA-CoA hydrolase |
| TE13 | A, B | paaI, paaD |
| TE14 | B, E | FatA, FatB |
| TE15 | B | Thioesterase CalE7 |
| TE16 | A, B, E | TE domain of FAS (Thioesterase I), TE domain of PKS or NRP (type I thioesterase (TE I)) |
| TE17 | B | TE domain of PKS |
| TE18 | B, E | Thioesterase II, type II thioesterase (TE II) |
| TE19 | B | luxD |
| TE20 | E | ppt1, ppt2, palmitoyl-protein thioesterase |
| TE21 | A, B, E | apt1, apt2, acyl-protein thioesterase, phospholipase, carboxylesterase |
| TE22 | A, B, E | S-formylglutathione hydrolase, esterase A, esterase D |
| TE23 | A, B, E | Hydroxyglutathione hydrolase, glyoxalase II |

[a]A, archaea; B, bacteria; E, eukaryota. Most prevalent producers bolded

It is also known to increase the secretion of fats into the culture medium, with for example acetic acid or HCL added to the medium to increase fatty acid production. This allows for easy collection of the fats by skimming. Collecting said fatty acids can also comprise collecting a solid fraction of said fatty acids by filtration of said medium; and extracting the remaining solids from the walls of said container with a hydrophobic solvent. Alternatively, collecting said fatty acids can comprises rinsing said walls with an alkali solution, and/or evaporating said hydrophobic solvent.

As used herein, "oxygen lean" conditions means 0.1-5% DO, or preferably about 0.2-0.5% DO, or about 0.5% DO.

As used herein, "oxygen rich" conditions means >20% DO, or preferably about 30-60 or about 40% DO.

As used herein, "anaerobic" conditions means <0.1% DO or even very close to 0%, although a true absence of oxygen is very difficult to achieve.

As used herein "DO profile control" refers to the use of a DO-stat or DO-meter to measure dissolved oxygen levels and automatically adjust the parameters so as to maintain a desired DO profile. Other method of controlling $O_2$ level include changing the level of agitation, changing the level of sparging, and changing the $O_2$ content of the sparging gas. To some extent, $O_2$ levels can also be controlled by controlling the number and activity of the microbes in the medium.

Oxygen saturation (symbol $S_{O2}$) is a relative measure of the amount of oxygen that is dissolved or carried in a given medium. It can be measured with a dissolved oxygen probe such as an oxygen sensor or an optode in liquid media, usually water. The standard unit of oxygen saturation is percent (%).

Dissolved oxygen (DO) is typically measured in standard solution units such as milligrams $O_2$ per liter (mg/L) or moles $O_2$ per cubic meter (mol/m$^3$). For example, in freshwater under atmospheric pressure at 20° C., $O_2$ saturation is 9.1 mg/L. However, DO can also be measured as a percent of saturation, which is done herein.

Dissolved oxygen meters consist of a DO probe connected to a meter/analyzer and are similar in construction to pH meters. The probe is comprised of two electrodes suspended in a potassium chloride (KCl) electrolyte solution, all of which is enclosed with glass and/or a semipermeable membrane. The electrodes are connected to the meter, which provides a small DC current to the electrodes via wiring. When the sensor is submerged in a liquid, oxygen from the liquid crosses the membrane and reacts with the cathode, causing a measurable current change; this change is converted into a millivolt output and is finally displayed by the meter.

Like pH instruments, dissolved oxygen meters typically measure more than DO. Multifunction meters may also measure pH, oxygen reduction potential (ORP), temperature, conductivity, and other liquid quality parameters. A DO-stat also contains the functionality of adjusting parameters so as to maintain a desired DO< or the provide a preprogrammed DO profile over time. Thus, with such a device is easily possible to smoothly transition from $O_2$ rich to $O_2$ lean conditions over a period of time.

Dissolved oxygen meters may be produced, tested, and used based on various standards. Example standards include:

ISO 5814—Water quality: determination of dissolved oxygen by electrochemical probe.

ASTM D888—Standard test methods for dissolved oxygen

BS EN 25813—Water quality: determination of dissolved oxygen by iodometric method As used herein, the expressions "microorganism," "microbe," "strain" "cell" and the like may be used interchangeably and all such designations include their progeny. It is also understood that all progeny may not be precisely identical in DNA content, due to deliberate or inadvertent mutations. Mutant progeny that have the same function and biological activity as screened for in the originally transformed cell are included. Where distinct designations are intended, it will be clear from the context.

As used herein, reference to a "cell," "microbe," etc. is generally understood to include a culture of such cells, as the work described herein is done in cultures having $10^{9-15}$ cells.

As used herein, "growing" cells used it its art accepted manner, referring to exponential growth of a culture of cells, not the few cells that may not have completed their cell cycle at stationary phase or have not yet died in the death phase or after harvesting.

As used in the claims, "homolog" means an enzyme with at least 40% identity to one of the listed sequences and also having the same general catalytic activity, although of course Km, Kcat, and the like can vary. While higher identity (60%, 70%, 80%) and the like may be preferred, it is typical for bacterial sequences to diverge significantly (40-60%), yet still be identifiable as homologs, while mammalian species tend to diverge less (80-90%).

Reference to proteins herein can be understood to include reference to the gene encoding such protein. Thus, a claimed "permease" protein can include the related gene encoding that permease. However, it is preferred herein to refer to the protein by standard name per ecoliwiki or HUGO since both enzymatic and gene names have varied widely, especially in the prokaryotic arts.

Once an exemplary protein is obtained, many additional examples of proteins with similar activity can be identified by BLAST search. Further, every protein record is linked to a gene record, making it easy to design overexpression vectors. Many of the needed enzymes are already available in vectors, and can often be obtained from cell depositories or from the researchers who cloned them. But, if necessary, new clones can be prepared based on available sequence information using RT-PCR techniques. Thus, it should be easily possible to obtain all of the needed enzymes/genes for overexpression.

Another way of finding suitable enzymes/genes for use in the invention is to consider other enzymes with the same EC number, since these numbers are assigned based on the reactions performed by a given enzyme. An enzyme can then be obtained, e.g., from AddGene or from the author of the work describing that enzyme, and tested for functionality as described herein or in the literature. In addition, many sites provide lists of proteins that all catalyze the same reaction.

Understanding the inherent degeneracy of the genetic code allows one of ordinary skill in the art to design multiple nucleotides that encode the same amino acid sequence. NCBI™ provides codon usage databases for optimizing DNA sequences for protein expression in various species. Using such databases, a gene or cDNA may be "optimized" for expression in *E. coli*, yeast, algal or other species using the codon bias for the species in which the gene will be expressed.

Initial cloning experiments have proceeded in *E. coli* for convenience since most of the required genes are already available in plasmids suitable for bacterial expression, but the addition of genes to bacteria is of nearly universal applicability. Indeed, since recombinant methods were invented in the 70's and are now so commonplace, even school children perform genetic engineering experiments using bacteria. Such species include e.g., *Bacillus, Streptomyces, Azotobacter, Trichoderma, Rhizobium, Pseudomonas, Micrococcus, Nitrobacter, Proteus, Lactobacillus, Pediococcus, Lactococcus, Salmonella, Streptococcus, Paracoccus, Methanosarcina*, and *Methylococcus*, or any of the completely sequenced bacterial species. Indeed, hundreds of bacterial genomes have been completely sequenced, and this information greatly simplifies both the generation of vectors encoding the needed genes, as well as the planning of a recombinant engineering protocol. Such species are listed along with links at http://en.wikipedia.org/wiki/List_of_sequenced_bacterial_genomes.

Additionally, yeasts, such as *Saccharomyces*, are a common species used for microbial manufacturing, and many species can be successfully transformed. Indeed, yeast are already available that express recombinant thioesterases-one of the enzymes described herein—and the reverse beta oxidation pathway has also been achieved in yeast. Other species include but are not limited to *Candida, Aspergillus, Arxula adeninivorans, Candida boidinii, Hansenula polymorpha (Pichia angusta), Kluyveromyces lactis, Pichia pastoris,* and *Yarrowia lipolytica,* to name a few.

It is also possible to genetically modify many species of algae, including e.g., *Spirulina, Apergillus, Chlamydomonas, Laminaria japonica, Undaria pinnatifida, Porphyra, Eucheuma, Kappaphycus, Gracilaria, Monostroma, Enteromorpha, Arthrospira, Chlorella, Dunaliella, Aphanizomenon, Isochrysis, Pavlova, Phaeodactylum, Ulkenia, Haematococcus, Chaetoceros, Nannochloropsis, Skeletonema, Thalassiosira,* and *Laminaria japonica,* and the like. Indeed, the microalga *Pavlova lutheri* is already being used as a source of economically valuable docosahexaenoic (DHA) and eicosapentaenoic acids (EPA), and *Crypthecodinium cohnii* is the heterotrophic algal species that is currently used to produce the DHA used in many infant formulas.

Furthermore, a number of databases include vector information and/or a repository of vectors and can be used to choose vectors suitable for the chosen host species. See e.g., AddGene.org, which provides both a repository and a searchable database allowing vectors to be easily located and obtained from colleagues. See also Plasmid Information Database (PlasmID) and DNASU having over 191,000 plasmids. A collection of cloning vectors of *E. coli* is also kept at the National Institute of Genetics as a resource for the biological research community. Furthermore, vectors (including particular ORFS therein) are usually available from colleagues.

The enzymes can be added to the genome (e.g. integrated) or added via expression vectors, as desired. Preferably, multiple enzymes are expressed in one vector or multiple enzymes can be combined into one operon by adding the needed signals between coding regions. Further improvements can be had by overexpressing one or more, or even all of the enzymes, e.g., by adding extra copies to the cell via plasmid or other vector. Initial experiments may employ expression plasmids hosting 3 or more ORFs for convenience, but it may be preferred to insert operons or individual genes into the genome for long term stability.

Alternatively, endogenous genes can be modified, by homologous recombination, recombineering, or gene editing, such as with CRISPR/CAS gene editing systems.

Still further improvements in yield can be had by reducing competing pathways, such as those pathways for making e.g., acetate, formate, ethanol, and lactate, and it is already well known in the art how to reduce or knockout these pathways. See e.g., the Rice patent portfolio by Ka-Yiu San and George Bennett (U.S. Pat. Nos. 7,569,380, 7,262,046, 8,962,272, 8,795,991) and patents by these inventors (U.S. Pat. Nos. 8,129,157 and 8,691,552) (each incorporated by reference herein in its entirety for all purposes). Many others have worked in this area as well.

In calculating "% identity" the unaligned terminal portions of the query sequence are not included in the calculation. The identity is calculated over the entire length of the reference sequence, thus short local alignments with a query sequence are not relevant (e.g., % identity=number of aligned residues in the query sequence/length of reference sequence). Alignments are performed using BLAST homology alignment as described by Tatusova T A & Madden T L (1999) FEMS Microbiol. Lett. 174:247-250, and available through the NCBI website. The default parameters were used, except the filters were turned OFF.

"Operably associated" or "operably linked", as used herein, refer to functionally coupled nucleic acid or amino acid sequences.

"Recombinant" is relating to, derived from, or containing genetically engineered material. In other words, the genetics of an organism was intentionally manipulated by the hand-of-man in some way.

"Reduced activity" is defined herein to be at least a 75% reduction in protein activity, as compared with an appropriate control species (e.g., the wild type gene in the same host species). Preferably, at least 80, 85, 90, 95% reduction in activity is attained, and in the most preferred embodiment, the activity is eliminated (100%). Proteins can be inactivated with inhibitors, by mutation, or by suppression of expression or translation, by knock-out, by adding stop codons, by frame shift mutation, and the like. All reduced activity genes or proteins are signified herein by "-".

By "null" or "knockout" what is meant is that the mutation produces undetectable active protein. A gene can be completely (100% or no detectable activity) reduced by knockout or removal of part of all of the gene sequence. Use of a frame shift mutation, early stop codon, point mutations of critical residues, or deletions or insertions, and the like, can also completely inactivate gene product by completely preventing transcription and/or translation of active protein. All null mutants herein are signified by "Δ."

"Overexpression" or "overexpressed" is defined herein to be at least 150% of protein activity as compared with an appropriate control species, or any detectable activity in a species that lacks the activity altogether. Preferably, the activity is increased 100-500% or even ten-fold. Overexpression can be achieved by mutating the protein to produce a more active form or a form that is resistant to inhibition, by removing inhibitors, or adding activators, and the like. Overexpression can also be achieved by removing repressors, adding multiple copies of the gene to the cell, or up-regulating the endogenous gene, and the like. All overexpressed genes or proteins are signified herein by "+".

In certain species it is possible to genetically engineer the endogenous protein to be overexpressed by changing the regulatory sequences or removing repressors. However, overexpressing the gene by inclusion on selectable plasmids or other vectors that exist in hundreds of copies in the cell may be preferred due to its simplicity and ease of exerting externals controls, although permanent modifications to the genome may be preferred in the long term for stability reasons.

The term "endogenous" or "native" means that a gene originated from the species in question, without regard to subspecies or strain, although that gene may be naturally or intentionally mutated, or placed under the control of a promoter that results in overexpression or controlled expression of said gene. Thus, genes from *Clostridia* would not be endogenous to *Escherichia*, but a plasmid expressing a gene from *E. coli* or would be considered to be endogenous to any genus of *Escherichia*, even though it may now be overexpressed.

"Wild type" means the gene's coding region is functional and as is found in nature.

"Expression vectors" are used in accordance with the art-accepted definition of a plasmid, virus or other propagatable sequence designed for protein expression in cells. There are thousands of such vectors commercially available, and typically each has an origin of replication (ori); a multiple cloning site; a selectable marker; ribosome binding sites; a promoter and often enhancers; and the needed termination sequences. Most expression vectors are inducible, although constitutive expression vectors also exist.

As used herein, "inducible" means that gene expression can be controlled by the hand-of-man, by adding e.g., a ligand to induce expression from an inducible promoter. Exemplary inducible promoters include the lac operon inducible by IPTG, the yeast AOX1 promoter inducible with methanol, the strong LAC4 promoter inducible with lactate, and the like. Low level of constitutive protein synthesis may occur even in expression vectors with tightly controlled promoters. Inducible genes, either integrated or on expression vectors, are preferred for use herein.

As used herein, an "integrated sequence" means the sequence has been integrated into the host genome in some fashion, as opposed to being maintained on an expression vector. It will still be expressible, and preferably is inducible as well.

The use of the word "a" or "an" when used in conjunction with the term "comprising" in the claims or the specification means one or more than one, unless the context dictates otherwise.

The term "about" means the stated value plus or minus the margin of error of measurement or plus or minus 10% if no method of measurement is indicated.

The use of the term "or" in the claims is used to mean "and/or" unless explicitly indicated to refer to alternatives only or if the alternatives are mutually exclusive.

The terms "comprise", "have", "include" and "contain" (and their variants) are open-ended linking verbs and allow the addition of other elements when used in a claim.

The phrase "consisting of" is closed, and excludes all additional elements.

The phrase "consisting essentially of" excludes additional material elements, but allows the inclusions of non-material elements that do not substantially change the nature of the invention, such as instructions for use, buffers, background mutations that do not effect the invention, and the like.

The following abbreviations are used herein:

| ABBREVIATION | TERM |
|---|---|
| ACP | acyl carrier protein |
| DO | Dissolved oxygen (%) |
| FAS | Fatty acid synthesis |
| RPM | Revolutions per minute |
| TE | Thioesterase |
| VVM | Volume of air under standard conditioner per liquid per minute |

DETAILED DESCRIPTION OF THE INVENTION

Figure 1:
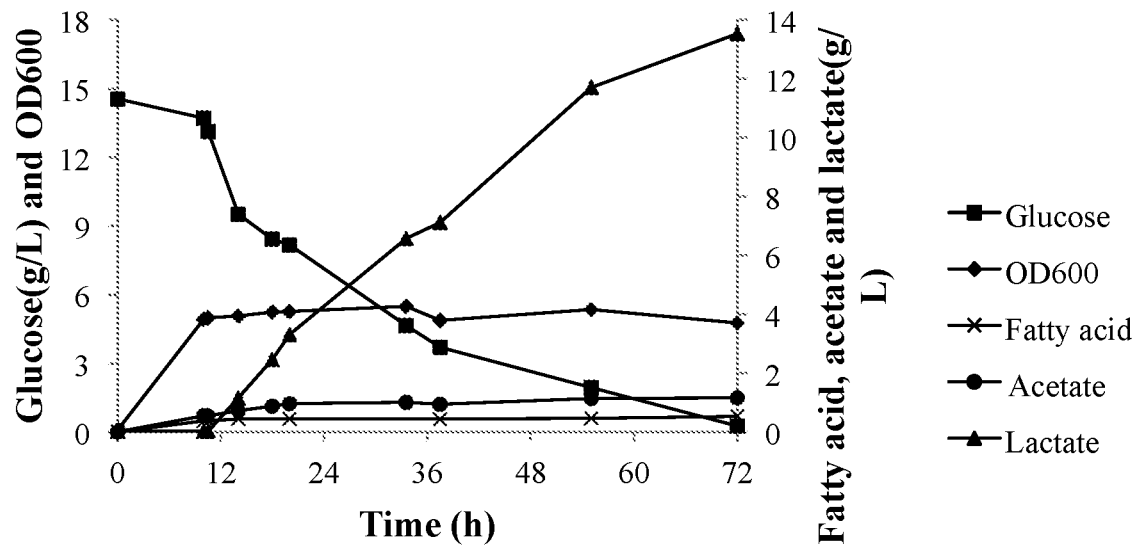
FIG. 1. Typical time profiles of strain ML103(pXZ18Z) cultivation: shift from 40% DO to 350 RPM and nitrogen stream after 10 hours.

A simple strategy to overcome the limitations of prior art aerobic culturing methods is to cultivate the cells aerobically. Under oxygen rich conditions, the cells are able to provide a plentiful supply of both ATP and NADH since the TCA cycle is active and the pyruvate dehydrogenase is functional. While this simple strategy will favor robust cell growth, it however leads to poorer fatty acid production. Oversupply of oxygen might lead to increased diversion of carbon source to carbon dioxide. In addition, active electron transfer chain (ETC), which uses oxygen as an electron acceptor, will drain NADH away from fatty acid synthesis. In brief, oversupply of oxygen will lead to lower fatty acid/carbon source yield.

This invention is about developing several strategies that can be used to overcome the NADH shortage problem. They are:

Approach 1: Cultivate the fatty acid producing strain under microaerobic or oxygen lean conditions to keep Pdh active to form necessary NADH from the conversion of pyruvate to acetyl-CoA.

Approach 2: Use of NADH-dependent formate dehydrogenase to regenerate NADH from formate.

Approach 3: Use of a mutant PDH that is more active under anaerobic or oxygen lean conditions (such as one that is insensitive to NADH feedback inhibition) or other enzyme such as pyruvate:ferredoxin oxidoreductase or similar system to regenerate NADH while converting pyruvate to acetyl-CoA under anaerobic conditions.

Approach 4: Introduce genes such as geranyl diphosphate: 4-hydroxybenzoate 3-geranyltransferase into fatty acid producing strain to attenuate ETC activity and economize the NADH usage under microaerobic conditions.

Combination of one or more of the above approaches are also possible, and they can also be combined with other gene modifications that further improve yields, such as various $TE^+$, $FabG^+$ and $FabZ^+$, and the like.

Experiments were conducted to demonstrate the performance of these various approaches. In particular, we demonstrated that the use of a two-stage approach which consists of an oxygen rich cell growth phase followed by an oxygen lean fatty acid production phase. We have also shown that $O_2$ mass transfer using only the headspace (and not bubbling through the media) is sufficient enough to provide enough oxygen in the second oxygen lean phase to yield much higher fatty acid production performance, and this has the benefit of eliminating foaming.

The strains ML103 (MG1655 ΔfadD) and ZL302 (ML103 P21::pTrc-lePGT) with plasmid pXZ18Z were used as examples. The plasmid pXZ18Z carried an acyl-ACP thioesterase (TE) and a fadZ gene from E. coli under the control of a trp promoter system. The proposed approach is equally application to any fatty acid production strains, although $O_2$ optima may vary between strains.

Transformation solution (50 μL) containing freshly transformed strains ML103 (MG1655 ΔfadD) or ZL302 (=ML103 P21::pTrc-lePGT) with plasmid pXZ18Z were spread on LB agar plate supplemented with 100 μg/mL ampicillin. The plates were then incubated at 37° C. for overnight. Several colonies were picked randomly from each plate and inoculated into 250 mL flasks containing 50 mL LB broth supplement with 100 μg/mL ampicillin. The flasks were then incubated in an orbital shaker at 37° C. and 250 RPM for 12-20 hours.

Batch fermentation experiments were performed in a 1-L bioreactor (BioFlo 110, New Brunswick Scientific Edison, N.J.) with 600 mL working volume. The fermentation medium contained 5 g/L yeast extract, 10 g/L tryptone and 10 g/L sodium chloride (LB broth) supplemented with 15 g/L glucose, 100 μg/mL ampicillin and 1 mM IPTG. The initial pH was adjusted to 7.2 with 2 N NaOH after autoclaving. Inoculum level was at 1 to 10% (v/v). The bioreactor was maintained at 30° C. The aeration rate was maintained at 1.0 vvm in the first phase using traditional sparging with filtered air unless stated otherwise.

Experiments were performed to demonstrate the importance of air/oxygen in the fatty acid production process. In this experiment, the dissolved oxygen (DO) of the bioreactor was first maintained at 40% by automatically changing the agitation speed (RPM) during the cell growth phase (initial 10 hours). Oxygen was supplied through a submerged gas sparger at a rate of 1.0 vvm with filtered air for the initial 10 hours.

The culture was then switched to anaerobic conditions by purging the headspace with sterile nitrogen gas at about 10 h. Typical time profiles using a free fatty acid producing strain ML103(pXZ18Z), a fadD inactivated MG1655 mutant strain with a plasmid carrying an acyl-ACP thioesterase and an E. coli fadZ gene, are shown in FIG. 1. The cells grew readily in the first 10 h reaching an optical density (OD600) about 5.5. However, the optical density (OD600) of culture did not increase further after switching to the anaerobic conditions after 10 h. The fatty acid concentration before the switch was about 0.36 g/L. The final fatty acid concentration reached only to about 0.50 g/L—an increase of merely 0.14 g/L during the anaerobic stage. A significant quantity of lactate was also accumulated at the end of the fermentation. This experiment clearly demonstrates the important of air (oxygen) for fatty acid production.

A set of bioreactor experiments were performed to show the significant effect of dissolved oxygen on fatty acid production. In these experiments, the DO concentrations in the bioreactor were maintained at a constant level by automatically changing the agitator speed (RPM). A summary of the results is shown in Table 3. A constant DO at 40% gives the highest fatty acid titer and yield. Under-supply of oxygen by setting the DO level too low led to a significant drop in fatty acid production performance—at 20% DO, the same strain has a fatty acid/sugar yield of only 0.168 g/g, which is approximately a 40% decrease. On the other hand, oversupply of oxygen also resulted in poorer fatty acid production.

TABLE 3

Comparison of batch fermentation of ML103(pXZ18Z) at constant DO on fatty acid production

| Fermentation condition | | FFA titer g/L | FFA yield g/g (FFA produced/ sugar utilized) | % Change* |
|---|---|---|---|---|
| Constant DO (%) | 20 | 2.52 | 0.168 | 39.29% |
| | 30 | 3.01 | 0.201 | 16.42% |
| | 40 | 3.51 | 0.234 | — |
| | 50 | 3.21 | 0.214 | 9.35% |
| | 60 | 3.22 | 0.215 | 8.84% |

* Comparisons using 40% DO as the reference.

Similar experiments were performed with constant RPM set at varying levels between 250 and 400 RPM and the results are summarized in Table 4. Again, fatty acid production and yield are very low at low RPM (limited mass transfer of oxygen). Hardly any fatty acid was produced at 250 RPM; this result is very similar to that of the anaerobic experiment shown in FIG. 1.

TABLE 4

Comparison of batch fermentation of ML103(pXZ18Z) at constant RPM on fatty acid production

| Fermentation condition | | FFA titer g/L | FFA yield g/g (FFA produced/ sugar utilized) | % Change* |
|---|---|---|---|---|
| Constant RPM | 250 | 0.07 | 0.005 | 4580.00% |
| | 280 | 2.07 | 0.138 | 69.57% |
| | 300 | 2.28 | 0.152 | 53.95% |
| | 350 | 2.37 | 0.158 | 48.10% |
| | 400 | 2.96 | 0.197 | 18.78% |

*Comparisons using 40% DO (Table 3) as the reference value

It is clear from the above set of experiments that oxygen supply is a very important factor in fatty acid production. A two-stage strategy was thus developed that consists of an initial oxygen rich growth phase to prepare the cells for fatty acid production (synthesis of abundant quantities of essential enzymes) and then followed by an oxygen lean (or even anaerobic) stage for maximal fatty acid production.

The results are summarized in Table 5. Reduction of DO to 20% in the second phase did not result in better fatty acid production performance. Similar amount of fatty acids were produced (Run #2). However, about 5% fatty acid production improvements were obtained when using a gradually decreasing DO profile control which was set to finish at a relatively low DO value (<5%) at the second phase (Run #3).

TABLE 5

DO profile control on fatty acid production

| | Conditions | | Total fatty acid | | |
|---|---|---|---|---|---|
| Run No. | First stage (before 10 h) | Second stage (after 10 h) | Total titer (g/L) | Total yield (g/g sugar) | % change |
| ML103(pXZ18Z): | | | | | |
| 1* | 40% DO | 40% DO | 3.51 | 0.234 | |
| 2 | 40% DO | 20% DO | 3.52 | 0.234 | |
| 3 | #DO profile | DO profile | 3.69 | 0.246 | 4.88 |

*From Table 3. #DO profile - A DO profile refers to a gradual drop of DO over the period of the initial 10 h from 100% at 0 hr to <5% at 10 hr. Oxygen was supplied through a submerged gas sparger at a rate of 1.0 VVM with filtered air through out the experiments, unless stated otherwise.

These results show that smoothly lowering the DO level to <0.5% in the second stage improved fatty acid productions levels.

A set of two-stage experiments were performed with the same fatty acid producing strains ML103(pXZ18Z). In this set of experiments, we further reduced the oxygen supply in the second oxygen lean stage by using headspace purging. This set of two-stage experiments, we used the same oxygen supply through a submerged gas sparger with air flowrate set at 1 vvm at the initial aerobic phase (10 hr or so) then switched to head space sparging. Using this method, we were able to get the DO level to about 0.5%.

Figure 2:
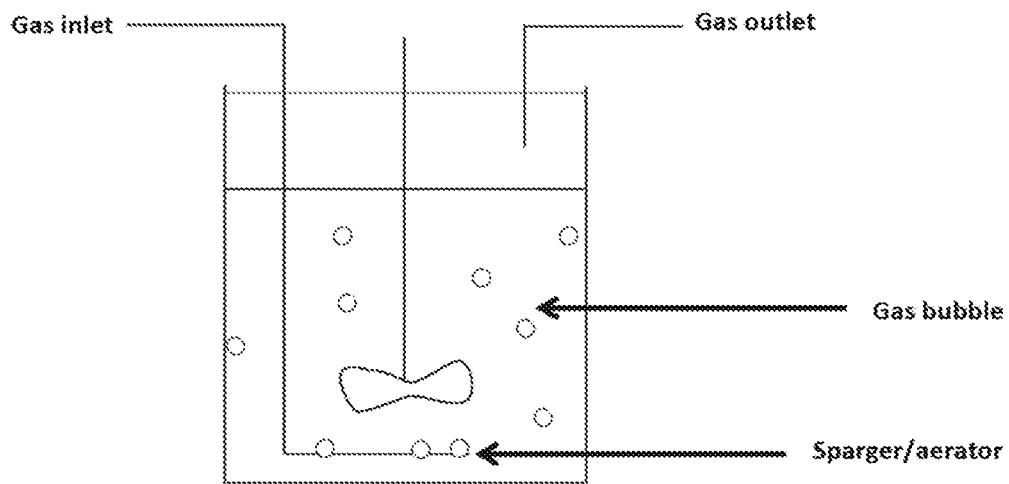
FIG. 2. Traditional sparging up through the culture media.

"Traditional aeration" is through a submerged sparger or aerator (see FIG. 2 below). Gas bubbles are formed through the sparger directly at or near the bottom of the culture medium, which great increase gas/liquid interfacial area. Agitation speed further influences the bubble size and thus the gas/liquid interfacial area. The problem with fatty acid production using this type of aeration is that it facilitates the formation of soap bubbles (foaming), which causes significant operating problems.

Figure 3:
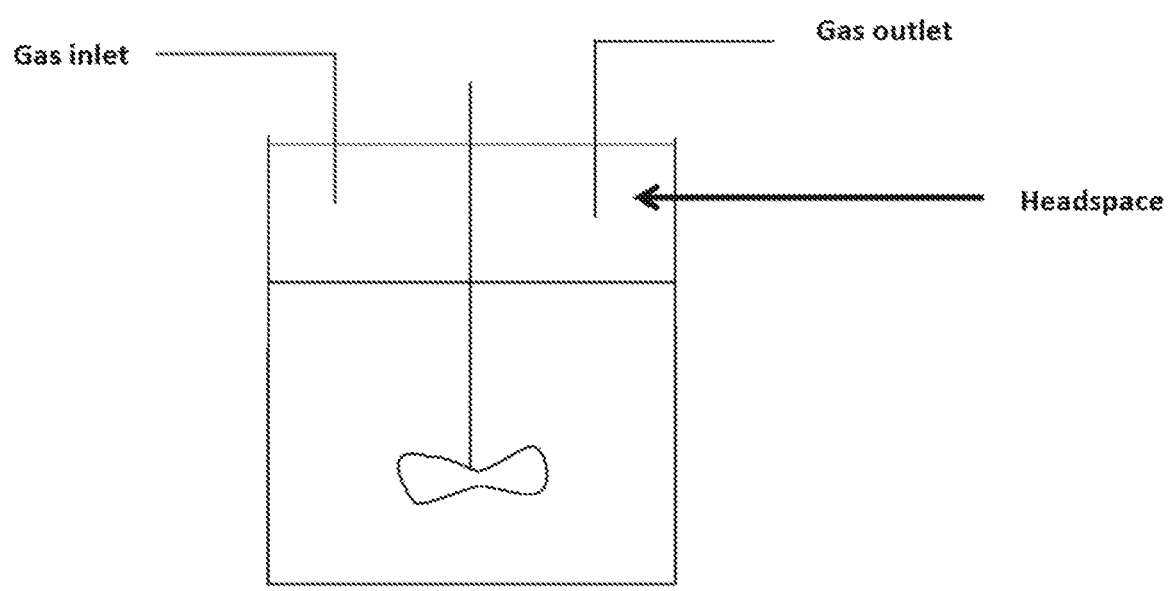
FIG. 3. Headspace sparging only via the headspace.

"Headspace aeration", as used herein, refers to gas supply only through the headspace of the bioreactor (see FIG. 3), as opposed to within the culture medium. "Headspace" is the space between the fermentation broth and the top of the reactor. In this operating mode, mass (oxygen) transfer is limited to the headspace/liquid contact area, and thus a far smaller DO is obtained in a simple and cost effective way. However, we have shown that such transfer rate is sufficient for the oxygen lean second stage of culturing.

Figure 4A:
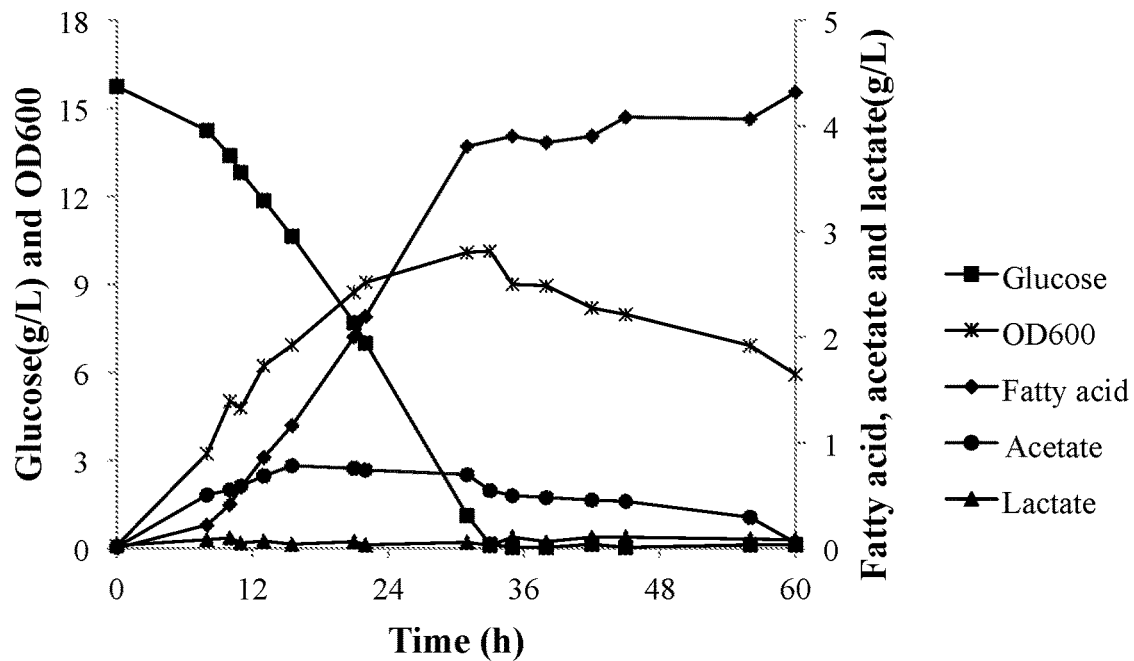
FIG. 4A Typical time profiles of strain ML103(pXZ18Z) cultivation.
Figure 4B:
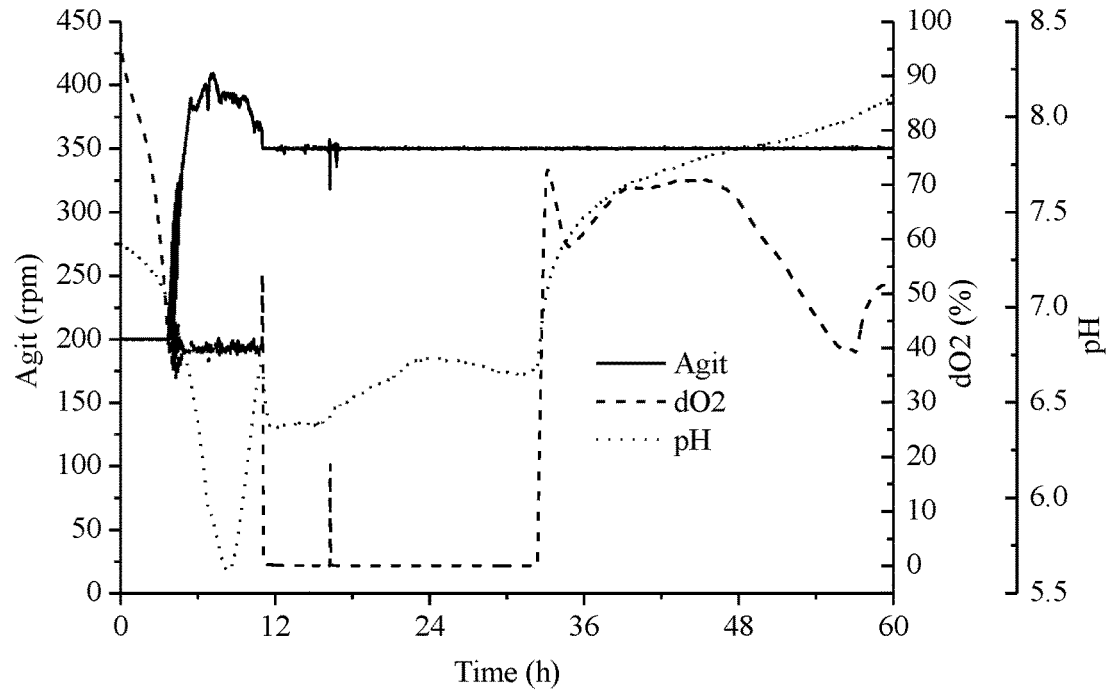
FIG. 4B Agitation (Agit) in RPM, pH and Oxygen levels; shift from 40% DO to 350 RPM after 10 hr (run #3 in Table 3). It is noted that DO initially drops significantly on entering the second phase of culturing, then increased. This is likely because the cells used up the carbon source (glucose) at around 33 hrs. Hence, the DO went up because they will then use less oxygen (the sparging continues the same as before).

A typical time profile is shown in FIG. 4. The results are summarized in Table 3. About 20% improvements in fatty acid production were achieved by using DO profile control in the first stage followed by headspace gas transfer approach with a DO set-point of 0.5% (Table 3 Run #1).

Further improvement of about 30% was obtained by using a constant agitation speed of 350 RPM in the second oxygen lean phase (Table 6 Run #2). The overall high yield value of 0.304 g/g is about 90% of the maximum theoretical yield value. It is important to point out that another major advantage of using headspace mass transfer is that it prevents any foam formation. As a result, no antifoam addition is needed (Table 3, runs 1-4). This is in sharp contrast with run 5 (Table 3) with traditional gas sparging by bubbling air or gas through the culture medium from below, where 33 ml of antifoam has to be added.

Strain ZL302(pXZ18Z) was constructed by integrating the geranyl diphosphate:4-hydroxybenzoate geranyl transferase from *Lithospermum erythrorhizon* (lePGT-1) into the chromosome of the strain ML103. The overexpression of lePGT-1 has shown to be able to control the electron transfer chain activity and regulate the cellular respiratory capacity in the presence of excessive air/oxygen supply.

The effect of overexpression of LePGT-1 on fatty acid production was examined first with a set of constant dissolved oxygen experiments (20 to 60%) and the results are summarized in Table 7. The strain ZL302 carrying the LePGT-1 outperformed its parent strain ML103 at all DO levels. The biggest improvement was for the 20% DO experiment, where a 35% increase in fatty acid production was observed. Strain ZL302 is also much less sensitive to the DO setting, similar amount of total fatty acids was obtained between 30 to 60% DO.

TABLE 7 comparison of ML103(pXZ18Z) and ZL302(pXZ18Z) - Constant DO control

| Dissolved Oxygen | Total fatty acids (g/L) ML103(pXZ18Z) | ZL302(pXZ18Z) | Percentage improvement |
|---|---|---|---|
| 20% | 2.52 | 3.41 | 35.32 |
| 30% | 3.01 | 3.62 | 20.27 |
| 40% | 3.51 | 3.62 | 3.13 |
| 50% | 3.21 | 3.65 | 13.71 |
| 60% | 3.22 | 3.56 | 10.56 |

Experiments were also performed to evaluate the performance of the strain ZL302 using the two-stage fermentation approach, which we have shown to yield much improved fatty acid performance as compared to the parent strain

TABLE 6

Microaerobic second phase improves fatty acid production (without pH control)

| | Conditions | | Total fatty acid | |
|---|---|---|---|---|
| Run No | First stage (before 10 h) | Second stage (after 10 h) | Total titer (g/L) | Total yield (g/g sugar) |
| | ML103(pXZ18Z): | | | |
| 1 | DO profile | headspace with air and 0.5% DO | 4.2 | 0.28 |
| 2 | DO profile | headspace with air and 350 rpm | 4.56 | 0.304 |
| 3 | 40% DO | headspace with air and 350 rpm | 4.32 | 0.288 |
| 4 | 20% DO | headspace with air and 350 rpm | 4.12 | 0.274 |
| 5 | 40% DO | 40% DO | 3.51 | 0.234 |

| | | | | Organic acids$_{max}$ | | | |
|---|---|---|---|---|---|---|---|
| Run No | % change | Base (mL) | Antifoam (mL) | Formate (g/L) | Acetate (g/L) | Ethanol (g/L) | Lactate (g/L) | Succinate (g/L) |
| | ML103(pXZ18Z): | | | | | | | |
| 1 | 19.56% | 0 | 0 | 0 | 0.86 | 0 | 0.19 | 0 |
| 2 | 29.91% | 0 | 0 | 0 | 0.87 | 0 | 0.15 | 0 |
| 3 | 23.08% | 0 | 0 | 0 | 0.8 | 0 | 0.11 | 0 |
| 4 | 17.38% | 0 | 0 | 0 | 0.58 | 0 | 0.13 | 0.15 |
| 5 | | 0 | 33 | 0 | 1.04 | 0 | 0.15 | 0 |

Figure 5A:
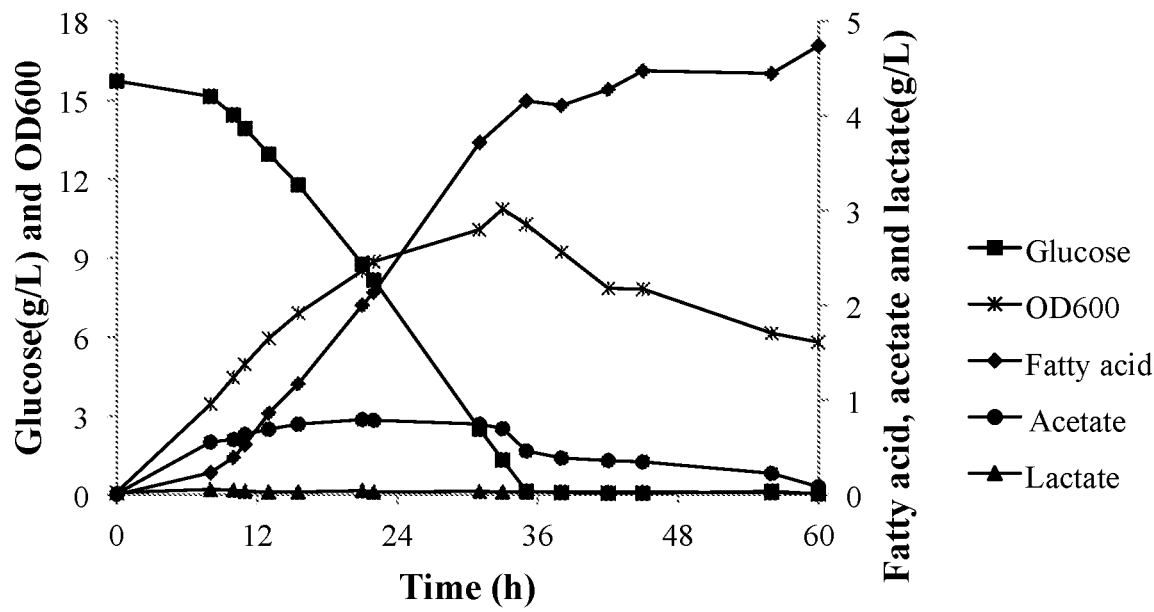
FIG. 5A Typical time profiles of strain Z302(pXZ18Z) cultivation.
Figure 5B:
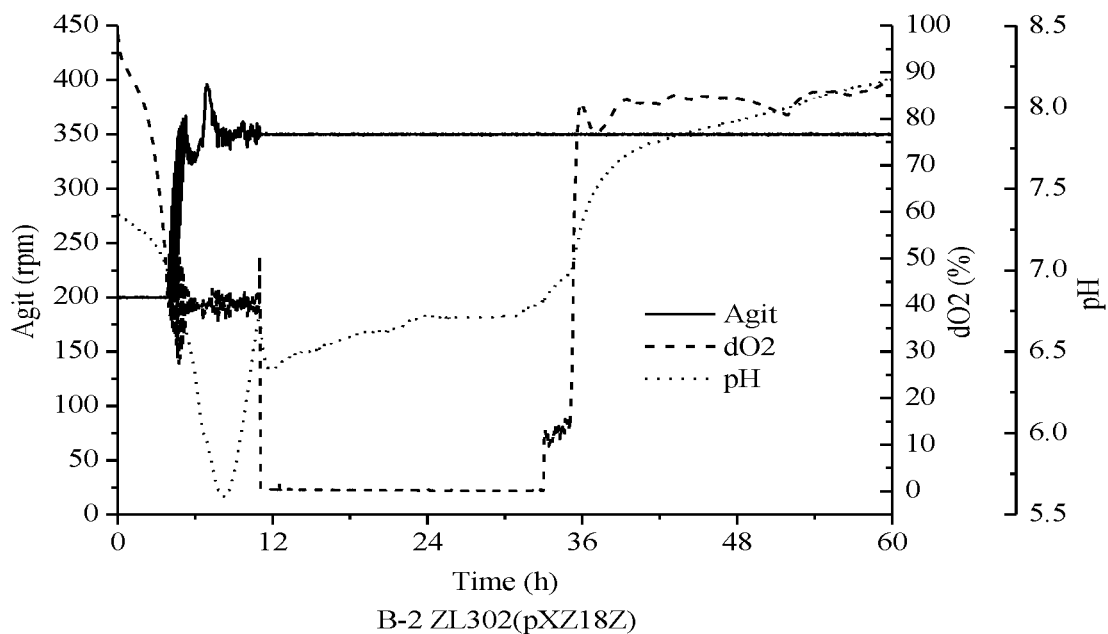
FIG. 5B Agitation (Agit) in RPM, pH and Oxygen levels; shift from 40% DO to 350 RPM after 10 hr.

ML103. A typical time profile is shown in FIG. 5, and the results are summarized in Table 8. Similar to the constant $O_2$ strategy, the strain ZL302 carrying the LePGT-1 outperformed its parent strain ML103, even under this improved approach. A very high yield of 0.316 g/g fat/sugar was obtained, which corresponds to more than 90% of the maximum theoretical yield.

Again, notice that no antifoam addition was needed when headspace gas transfer approach was used. On the other hand, the experiments with 20% DO in the second phase (gas bubbling), large quantities of antifoam have to be added to prevent foam formation (86 and 118 ml, respectively, Table 8).

The control strain GJT(pXZ18) carrying a plasmid harboring an acyl-ACP thioesterase did not produce appreciable quantity of fatty acids, yielding only 0.027 g/L. On the other hand, the genetically engineering host GJT:FDH with one set of NAD-dependent fdh gene from *Candida boidinii* (Uniprot O13437) integrated into the chromosome under the control of an IPTG inducible pTrp promoter system produced significantly more fatty acids, 0.103 g/L, which represents more than 280% improvement over the control.

Increasing the gene dosage from one to two then to three copies of NAD-dependent fdh gene further increases the

TABLE 8 comparison of ML103(pXZ18Z) and ZL302(pXZ18Z) - two stage approach

| | Conditions | | Total fatty acid | | |
| --- | --- | --- | --- | --- | --- |
| strain | First stage (before 10 h) | Second stage (after 10 h) | Total titer (g/L) | Total yield (g/g sugar) | % improvement |
| ML103 (pXZ18Z) | 40% DO | headspace with air and 350 rpm | 4.32 | 0.288 | — |
| | 40% DO | 20% DO | 3.52 | 0.234 | — |
| ZL302 (pXZ18Z) | 40% DO | headspace with air and 350 rpm | 4.74 | 0.316 | 9.72 |
| | 40% DO | 20% DO | 4.24 | 0.282 | 20.45 |

| | | Organic acids$_{max}$ | | | |
| --- | --- | --- | --- | --- | --- |
| strain | Antifoam (mL) | Formate (g/L) | Acetate (g/L) | Ethanol (g/L) | Lactate (g/L) | Succinate (g/L) |
| ML103 (pXZ18Z) | 0 | 0 | 0.80 | 0 | 0.11 | 0 |
| | 86 | 0 | 0.55 | 0 | 0.12 | 0 |
| ZL302 (pXZ18Z) | 0 | 0 | 0.79 | 0 | 0 | 0 |
| | 118 | 0 | 0.66 | 0 | 0 | 0 |

Experiments were performed to demonstrate the importance of overexpression of a NAD-dependent formate dehydrogenase (FDH) on fatty acid production. The enzyme NAD-dependent FDH is capable of regenerating NADH from NAD upon the conversion of formate to carbon dioxide. This is in contrast with the *E. coli* native formate dehydrogenase, which converts formate to carbon dioxide and hydrogen. Examples of suitable enzymes are found at E.C. 1.2.1.2.

amount of fatty acids produced (Table 9). The engineering strain with three copies of the NAD-dependent fdh gene into the host chromosome produced 0.325 g/L of fatty acids, which is about 1,100% improvement over the control strain (Table 9).

In summary, these sets of experiments clearly demonstrate overexpression of a NAD-dependent formate dehydrogenase (FDH) enables the strain to produce significant fatty acid under strict anaerobic conditions.

TABLE 9

Importance of overexpression of a NAD-dependent formate dehydrogenase (Fdh) on fatty acid production

| Strain | Relevant genotype | Fatty acid produced (g/L) | Percentage improvement |
| --- | --- | --- | --- |
| GJT(pXZ18) | Host strain GJT, an *E. coli* K12 derivative, carrying a plasmid harboring an acyl-ACP thioesterase | 0.027 | — |
| GJT:FDH (pXZ18) | Modified host strain GJT with chromosomal integration of one copy of a NAD-dependent formate dehydrogenase; this host also carries a plasmid harboring an acyl-ACP thioesterase | 0.103 | 281% |
| GJT:2FDH (pXZ18) | Modified host strain GJT with chromosomal integration of two copies of a NAD-dependent formate dehydrogenase; this host also carries a plasmid harboring an acyl-ACP thioesterase | 0.138 | 411% |

TABLE 9-continued

Importance of overexpression of a NAD-dependent formate dehydrogenase (Fdh) on fatty acid production

| Strain | Relevant genotype | Fatty acid produced (g/L) | Percentage improvement |
|---|---|---|---|
| GJT:3FDH (pXZ18) | Modified host strain GJT with chromosomal integration of three copies of a NAD-dependent formate dehydrogenase; this host also carries a plasmid harboring an acyl-ACP thioesterase | 0.325 | 1104% |

Similar experiments were performed to demonstrate the role of overexpression of a NAD-dependent formate dehydrogenase (FDH) on fatty acid production under different genetic backgrounds. In these experiments, the engineering host with 3 copies of NAD-dependent fdh gene, GJT:3FDH, was used and its performance was compared with its parent strain GJT.

In the first experiment, both strains carried a plasmid carrying an acyl-ACP thioesterase, NAD-dependent fabG gene and an *E. coli* fabZ gene. The control strain produced only 0.031 g/L of fatty acids, while the engineered strain with 3 copies of NAD-dependent fdh gene plus FabG plus FabZ produces 0.413 g/L of fatty acids, which represents more than 1200% improvement (Table 10, rows 1 and 2).

In the second experiment, a thioesterase Tes'A from *E. coli* together with an *E. coli* fabZ were used. Similar to previous experiments, the engineered strain with 3 copies of NAD-dependent fdh gene plus Tes'A plus FabZ showed an improvement of more than 550% over the control strain (Table 10, rows 3 and 4).

In summary, these sets of experiments clearly demonstrate overexpression of a NAD-dependent FDH enables the strain to produce fatty acid under strict anaerobic conditions under various genetic backgrounds.

Prophetic Experiments

Similar experiments will be performed with a fatty acid producing strain carrying a NAD-dependent formate dehydrogenase with decreasing supply of oxygen till all the way to fully anaerobic conditions. Since the NAD-dependent formate dehydrogenase has shown to be able to increase NADH availability by regenerating NADH from formate under anaerobic conditions, this experiment is predicted to be successful.

Similar experiments will be performed using a fatty acid producing strain with NADH feedback insensitive pyruvate dehydrogenase (either chromosomally or extra-chromosomally using an expression vector) under decreasing supply of oxygen till all the way to fully anaerobic conditions. Since the NADH feedback insensitive pyruvate dehydrogenase has been shown to retain its enzymatic activity under anaerobic condition, this experiment is predicted to be successful. Examples of suitable enzymes can be constructed as described in Sun (2012).

Similar experiments will be performed using a fatty acid producing strain carrying NAD-dependent 3-oxoacyl-ACP reductase (FabG) (with reduced or inactivated native NADP-dependent 3-oxoacyl-ACP reductase activity) under decreasing supply of oxygen till all the way to fully anaero-

TABLE 10

Importance of overexpression of a NAD-dependent formate dehydrogenase (Fdh) on fatty acid production under different genetic backgrounds

| Strain | Relevant genotype | Fatty acid produced (g/L) | Percentage improvement |
|---|---|---|---|
| GJT(pXZ18G2Z) | GJT carries a plasmid harboring an acyl-ACP thioesterase, NAD-dependent fabG gene and an *E. coli* fabZ gene. This strain served as a control | 0.031 | — |
| GJT:3FDH (pXZ18G2Z) | Modified host strain GJT with chromosomal integration of three copies of a NAD-dependent formate dehydrogenase; this host also carries a plasmid harboring an acyl-ACP thioesterase, NAD-dependent fabG gene and an *E. coli* fabZ gene. | 0.413 | 1232% |
| GJT(pXZtes'AZ) | GJT carries a plasmid harboring an *E. coli* tes'A gene and an *E. coli* fabZ gene. This strain is served as control | 0.072 | — |
| GJT:3FDH (pXZtes'AZ) | Modified host strain GJT with chromosomal integration of three copies of a NAD-dependent formate dehydrogenase; this host also carries a plasmid harboring an *E. coli* tes'A gene and an *E. coli* fabZ gene. | 0.482 | 569% | bic conditions. Since NAD-dependent 3-oxoacyl-ACP reductase use NADH, which is much more abundant than that of NADPH, this experiment is predicted to be successful. Examples of suitable enzymes are found at Acc. No. Rv0242c.

Each of the following is incorporated by reference herein in its entirety for all purposes:
US20140093921 Bacteria and method for synthesizing fatty acids
US20140193867 Microbial odd chain fatty acids
US20140193867 Microbial odd chain fatty acids
US20140212935 Short chain fatty acids from bacteria
US20140273114 Bacteria and method for synthesizing fatty acids
U.S. Pat. No. 7,326,557 Increasing intracellular NADPH availability in *E. coli*
U.S. Pat. No. 7,901,924 Increased bacterial CoA and acetyl-CoA pools
U.S. Pat. No. 8,129,157 Anaerobic fermentation of glycerol
U.S. Pat. No. 8,486,686 Large scale microbial culture method
U.S. Pat. No. 8,691,552 Microaerobic cultures for converting glycerol to chemicals
WO2015054138 Improved fatty acid productivity
Olsson J. & Andrews J. F., The dissolved oxygen profile-A valuable tool for control of the activated sludge process, Water Research, 12(11): 985-1004 (1978).
Sun Z, et al. Amino acid substitutions at glutamate-354 in dihydrolipoamide dehydrogenase of *Escherichia coli* lower the sensitivity of pyruvate dehydrogenase to NADH. Microbiology. 2012 May; 158(Pt 5):1350-8
Wu H, Tuli L, Bennett G N, San K Y. Metabolic transistor strategy for controlling electron transfer chain activity in *Escherichia coli*. Metab Eng. 28:159-168 (2015)
Zhang X, Li M, Agrawal A, San K Y, Efficient free fatty acid production in *Escherichia coli* using plant acyl-ACP thioesterases, Metab Eng. 13(6):713-22 (2011).

The invention claimed is:

1. A method of producing products in bacteria, comprising:
   a) aerobically culturing a bacteria in a growth medium until sufficient cell mass is reached;
   b) smoothly transitioning from aerobic culturing to culturing under oxygen lean conditions (>0.1% dissolved oxygen ("DO") to <5% DO) over a course of time of 1-12 hrs;
   c) further culturing said bacteria under oxygen lean conditions by only sparging a head space with $O_2$ containing gas until product is formed; and
   d) isolating said product from said bacteria, said growth medium, or both.

2. The method of claim 1, wherein step a) further comprises aerobically culturing said bacteria with about 40% DO until >75% of maximal cell mass is reached.

3. The method of claim 1, wherein steps a)-c) further comprise:
   a) aerobically culturing said bacteria in the growth medium with about 40% DO until an $OD_{600}$ of >2 or >5 is reached;
   b) smoothly transitioning from about 40% DO to about 0.5% DO over said course of time;
   c) further culturing said bacteria with about 0.5% DO at about 350 rpm and only sparging the headspace with air until product is formed.

4. The method of claim 1, wherein steps a) and c) further comprise:
   a) aerobically culturing said bacteria in the growth medium until >75 to <95% maximum cell mass before stationary phase is reached;
   c) further culturing said bacteria with oxygen lean conditions and agitation at about 350 rpm and only sparging the head space with air until products are formed.

5. The method of claim 1, wherein less pH control is used in said method than in a comparable method without said head space sparging.

6. The method of claim 1, wherein said product is derived from a fatty acid synthesis cycle, and said bacteria comprises overexpressed LePGT-1.

7. The method of claim 1, wherein said product is a fatty acid and said bacteria comprises a mutant pyruvate dehydrogenase that is active under 0.5% DO conditions.

8. The method of claim 1, wherein both aerobic and oxygen lean culturing is done in a single bioreactor.

9. The method of claim 1, wherein said product is a fatty acid and said bacteria comprises at least one of:
   i) an overexpressed NADH-dependent formate dehydrogenase, and NADH insensitive pyruvate dehydrogenase or pyruvate:ferredoxin oxidoreductase or NADH-dependent 3-oxoacyl-ACP reductase (FabG);
   ii) reduced expression of one or more enzymes for the production of lactate, acetate, formate or ethanol;
   iii) an overexpressed TE;
   iv) an overexpressed TE and overexpressed PGT-1;
   v) an overexpressed TE and overexpressed NADH-dependent formate dehydrogenase (FDH); and
   vi) an overexpressed TE, an overexpressed NADH-dependent FDH and an overexpressed PGT-1.

* * * * *